United States Patent [19]

Buget et al.

[11] Patent Number: 4,838,676
[45] Date of Patent: Jun. 13, 1989

[54] OPTICAL DEVICE FOR MEASURING THE POSITION OF THE MAIN OR OTHER DIRECTIONS OF VISION OF BOTH EYES, AND ANOMALIES IN BINOCULAR VISION

[75] Inventors: Bernard Buget, 16 Place de l'Alma, 57600 Forbach; Etienne Maurice, Rupt-sur-Moselle, both of France

[73] Assignee: Bernard Buget, Forbach, France

[21] Appl. No.: 28,381

[22] Filed: Mar. 19, 1987

[30] Foreign Application Priority Data

Mar. 19, 1986 [EP] European Pat. Off. ........ 86400578.0

[51] Int. Cl.⁴ ................................................ A61B 3/10
[52] U.S. Cl. ..................................... 351/202; 351/204
[58] Field of Search ....................... 351/201, 204, 202; 33/200

[56] References Cited

U.S. PATENT DOCUMENTS 4,208,800 6/1980 Grolman et al.
4,368,958 1/1983 Buget ................................. 351/204

FOREIGN PATENT DOCUMENTS 2444631 1/1976 Fed. Rep. of Germany.
458911 8/1968 Sweden.

Primary Examiner—Rodney B. Bovernick
Assistant Examiner—Jay Ryan
Attorney, Agent, or Firm—Young & Thompson

[57] ABSTRACT

An optical device can be fitted in front of a patient's eyes and comprises a holder (1) bearing two movable screens (2, 3) of transparent polarizing material. The two screens (2, 3) are moved in front of the eyes, and their position relative to the holder (1) of the device is determined. A target is separated from the holder and is adapted to be placed in front of the patient so as to be visible to the latter, a central part of the target having a polarization axis perpendicular to that of the polarizing screens (2, 3). Each polarizing screen (2, 3), near its lateral edge (2a, 3a) nearest the axis of symmetry (Y, Y') extending between the two screens, has a slot (5a, 6a) substantially parallel to the aforementioned axis of symmetry, whereas near its bottom edge (2b, 3b) it has a slot (5b, 6b) substantially perpendicular to the previously-mentioned slot. The two screens (2, 3) are moved in such a way that the slots (5a, 6a; 5b, 6b) in the screens remain parallel to themselves when the screens move.

14 Claims, 5 Drawing Sheets

FIG_1

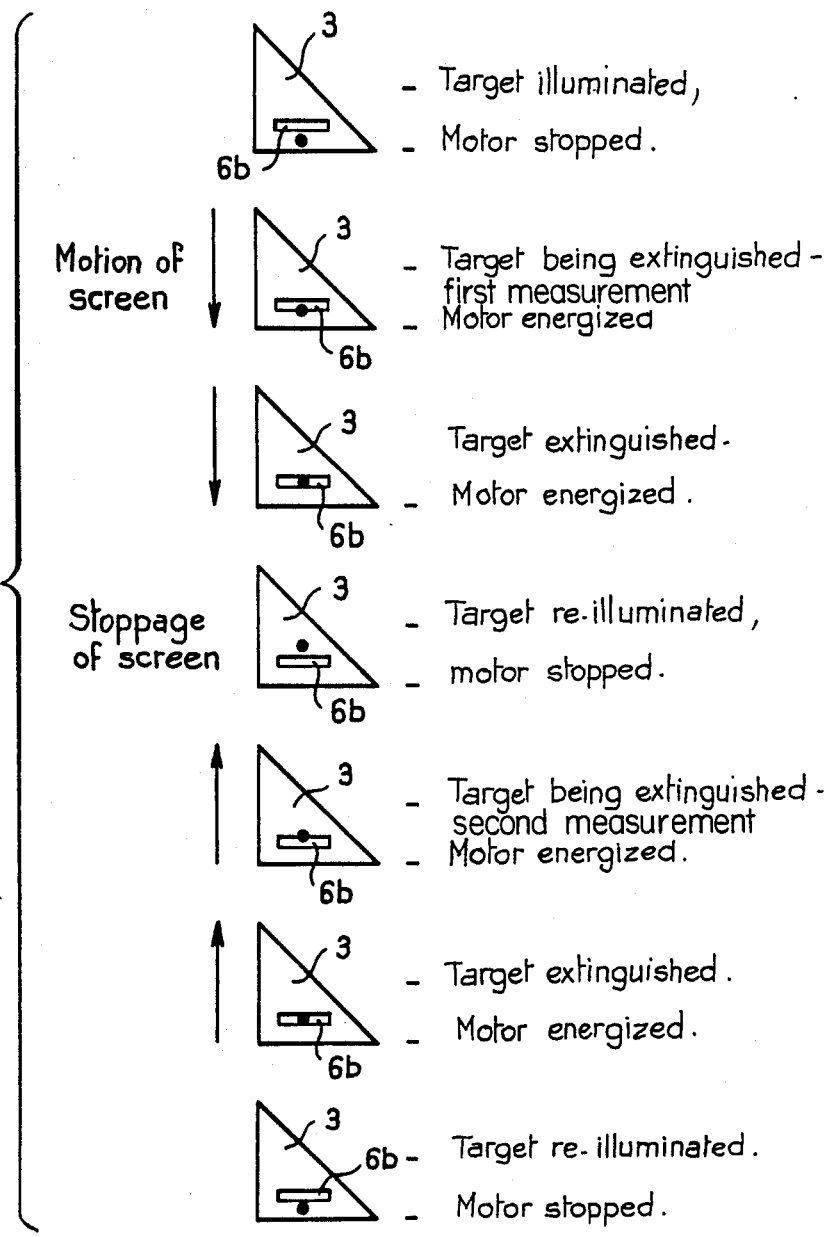

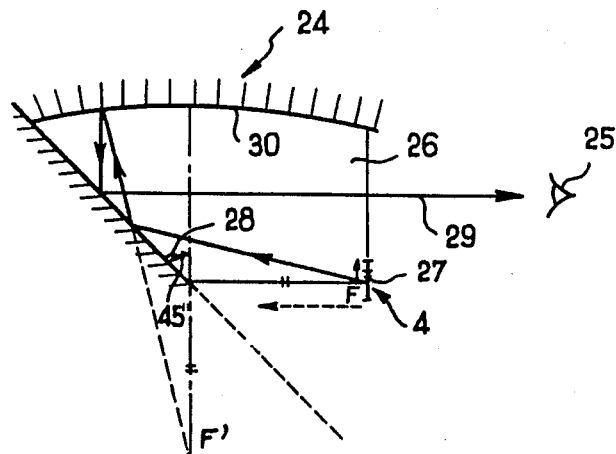
FIG_8
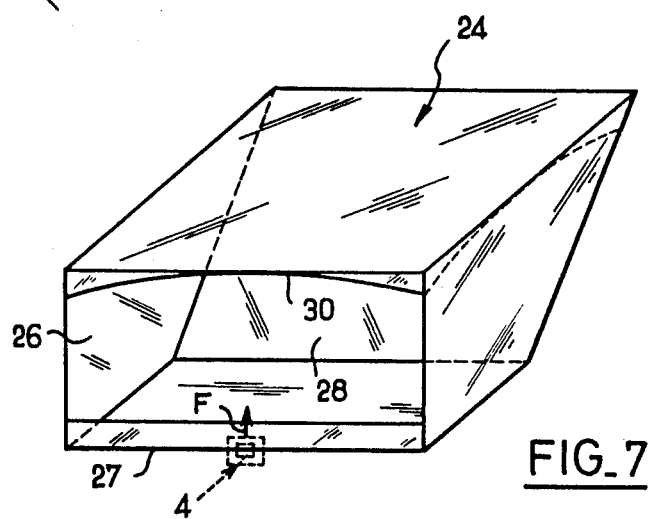
FIG_7
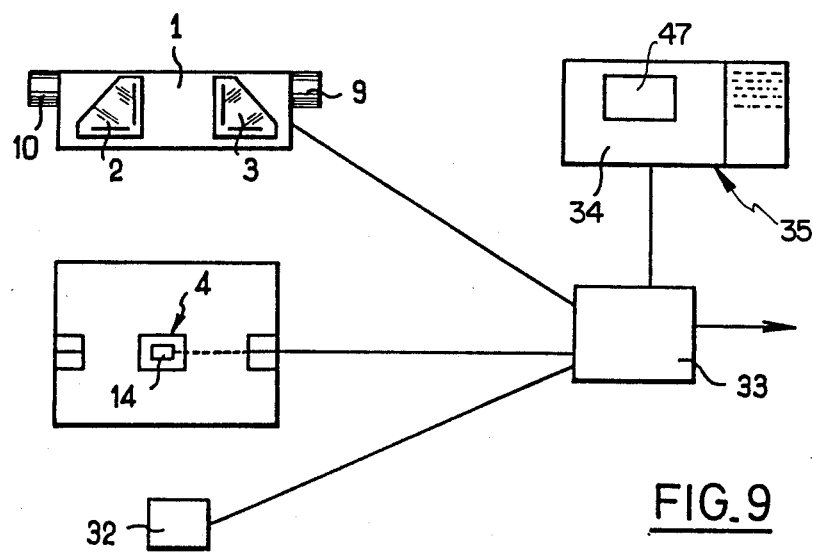
FIG_9

_(1)_

OPTICAL DEVICE FOR MEASURING THE POSITION OF THE MAIN OR OTHER DIRECTIONS OF VISION OF BOTH EYES, AND ANOMALIES IN BINOCULAR VISION

BACKGROUND OF THE INVENTION

The invention relates to an optical device for measuring the position of the main or other directions of vision of both eyes and for measuring anomalies in binocular vision.

In the absence of anomalies in binocular vision or in the case of monocular vision, the position of the directions of vision of both eyes measured by the device is the position of the main directions or axes of vision.

OBJECTS OF THE INVENTION

As is known, the position of the axes of vision of both eyes must be known in order properly to mount two corrective lenses in a spectacle frame, the optical centres of the lenses usually being situated along the axes of vision of the eyes.

The Applicants, in their U.S. Pat. No. 4,368,958, describe an optical device for fitting in front of a patient's eyes and very accurately locating the positions of the axes of vision of both eyes.

The device comprises a holder bearing two screens of transparent, polarizing material movable in translation, means being provided for moving the two screens in front of the eyes and locating the position thereof relative to the holder.

The aforementioned device also comprises a target separate from the holder and disposed at a certain distance in front of the patient so as to be visible to him. The target has a central reference mark covered by a screen having an axis of polarization perpendicular to that of the polarizing screens borne by the holder. The mark covered by the polarizing screen is surrounded by a non-polarizing reference area.

When the polarizing screens borne by the holder intersect the axis of vision of an eye, the patient's eye in question cannot see the mark on the target. On the other hand, when an edge of the polarizing screen placed in front of the eye is disposed near the aforementioned axis of vision, the patient begins to see the central mark on the target. In this manner, by successively moving the polarizing screens so that their vertical and horizontal edges coincide with the axis of vision of each eye, it is possible to accurately determine the position of the axes of vision of both eyes relative to the holder, while ensuring that both eyes continue to converge onto the non-polarizing reference zone.

The aforementioned device has the disadvantage that the optician has to move the polarizing screens in two perpendicular directions in succession by hand, so that the device is complicated to use and subject to errors due to confusion.

One object of the invention is to obviate this disadvantage by producing a device which is simpler to use and can automatically and more accurately determine the position of the directions of vision of both eyes of a patient.

Another object is to use the aforementioned device to measure anomalies in binocular vision, such as squinting.

At present, anomalies in binocular vision are discovered by placing a dissociating optical device in front of the patient's eyes. The optician asks the patient to stare at a light source disposed at the centre of a graduated cross, called a Madox cross.

If there are anomalies in binocular vision, the point image of the light source on the retina of one eye does not correspond to the same point image on the retina of the other eye; the result for the patient is a double image or diplopia.

Since the corresponding points on the retina have the same direction of vision, a deflection of the direction of vision measured by the optician is found as follows:

the two images are re-centred, by disposing prisms of suitable optical characteristics in front of the eye, or the deflection is recorded directly on the Madox cross by asking the patient to read those graduations on the cross which are opposite the image, which has been deflected from the centre of the cross.

In both cases there is a dialogue with the patient. As can be seen, this method of operation may result in errors due to mistakes by the patient when reading the graduations.

The device according to the invention can obviate all the shortcomings of the prior art as described hereinbefore.

SUMMARY OF THE INVENTION

The invention relates to an optical device for measuring the position of the main or other directions of vision of the two eyes and for measuring anomalies in binocular vision, the device being adapted for fitting in front of the patient's eyes and comprising a holder bearing two movable screens of transparent polarizing material, means for moving the two screens in front of the eyes, means for locating the position of the screens relative to the holder, and a target separated from the holder and adapted to be placed in front of the patient, the target comprising a central area having an axis of polarization perpendicular to that of the polarizing screens.

According to the invention, the device is characterised in that each polarizing screen, near its side edge nearest to the axis of symmetry of the holder extending between the two screens, has a slot substantially parallel to the aforementioned axis of symmetry whereas near its bottom edge it has a slot substantially perpendicular to the aforementioned slot and the means for moving the two screens comprise a single actuating component for each screen, cooperating with transmission means such that the slots in the screens remain parallel to themselves when the screens move.

The target is visible to the patient when the direction of vision extends through one of the slots in a polarizing screen. These slots can be used for accurately locating the position of the directions of vision relative to the axis of symmetry of the holder extending between the two screens, and relative to an axis perpendicular to the first-mentioned axis.

Furthermore, since each polarizing screen is moved by a single actuating component, the device according to the invention is much easier to construct and use than the known device described hereinbefore.

In an advantageous embodiment of the invention, each polarizing screen is connected to the holder by two parallel arms jointed to the screen and to the holder and the pivot joining one of the arms to the holder is connected to a motor so as to rotate the pivot, the pivot being secured to a toothed sector engaging a toothed sector mounted on the motor output shaft.

When the motor rotates, the two arms rotate around their two pivots secured to the holder and the polarizing screen borne by the arms moves in front of the holder so that the slots in the screen always remain parallel to themselves.

In a preferred embodiment, the means for moving the two screens and the transmission means are adapted to move the two screens between a first position where the bottom edge of the screens is disposed above the direction of vision of the two eyes, a second position in which the slot situated near the bottom edge of each screen is in the direction of vision of the corresponding eye when turned towards the target, and a third position in which the slot near the side edge of each screen is in the aforementioned direction of vision.

Preferably, the motor for moving the polarizing screens is associated with means for locating the position of the slot near the bottom edge of each screen with respect to a horizontal reference axis of the holder, and for locating the position of the slot near the side edge of each screen relative to a reference position perpendicular to the previously-mentioned reference and extending along the axis of symmetry of the holder between the two polarizing screens.

The holder of the device according to the invention can comprise means for securing it to test spectacles for examinations of binocular vision.

Alternatively the holder can be independent and comprise means for directly securing it to the patient's eyes without interposed spectacles, and means whereby corrective lenses or others useful for the examination are secured in front of the holder.

The holder can also comprise means for securing it to the patient's spectacle frame.

Other features and advantages of the invention will be clear from the following description.

BRIEF DESCRIPTION OF THE FIGURES

In the accompanying drawings, given by way of non-limitative example:

FIG. 6 is a diagram showing the various positions of a polarizing screen during a measurement;

FIG. 7 is a three-fourths perspective front view of a casing holding a target forming part of the device according to the invention;

FIG. 8 is a diagrammatic view in longitudinal section of the casing, showing its operation, and FIG. 9 is a diagram showing the device according to the invention and the target associated with a microcomputer.

DETAILED DESCRIPTION

Figure 1:
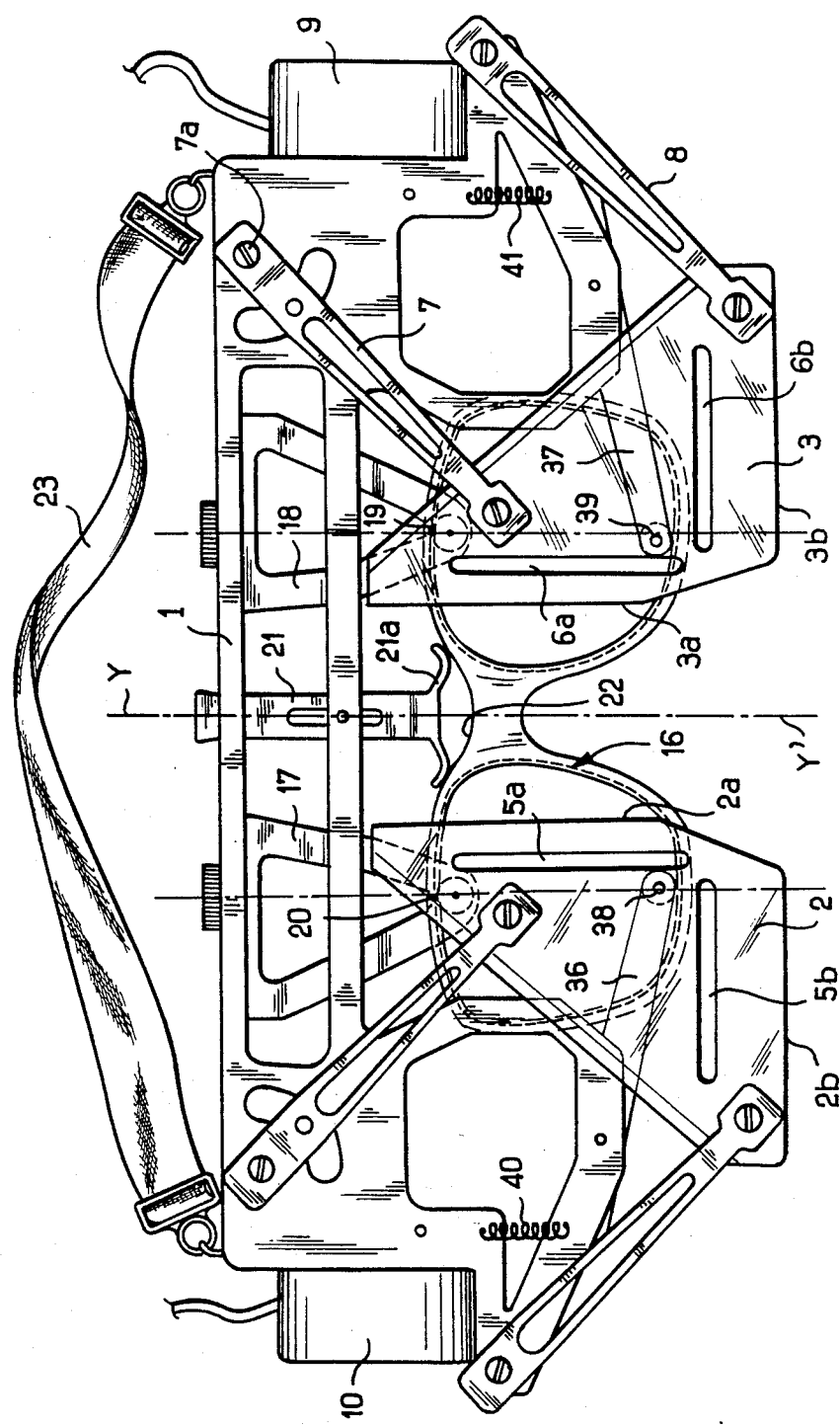
FIG. 1 is a plan view showing the front of a device according to the invention secured to a spectacle frame.

The embodiment in FIG. 1 shows an optical device for measuring the position of the main or other directions of vision of both eyes and for measuring anomalies in binocular vision and adapted to be fitted in front of the patient's eyes. The device comprises a light-alloy or plastics holder 1 bearing two movable screens 2, 3 of transparent polarizing material, means described hereinafter for moving the two screens in front of the two eyes, and means for locating the position of the screens 2, 3 relative to the holder 1.

The device also comprises a target 4 (see FIG. 3) separated from the holder 1 and adapted to be placed in front of the patient so as to be visible to him. The target, at the centre of a non-polarized reference area 15, has an area 14 having an axis of polarization perpendicular to that of the polarizing screens 2 and 3.

Each screen 2 and 3, near its side edge 2a, 3a, nearest the axis of symmetry Y—Y' extending between screens 2 and 3, has a slot 5a, 6a substantially parallel to the aforementioned axis of symmetry, whereas near its bottom edge 2b, 3b it has a slot 5b, 6b perpendicular to slot 5a, 6a. Slots 5a, 6a; 5b, 6b have a width of a few tenths of a mm.

The means for moving each screen 2, 3 comprise a single actuating component co-operating with transmission means such that slots 5a, 6a; 5b, 6b remain parallel to themselves when screens 2, 3 move.

Figures 2, 3:
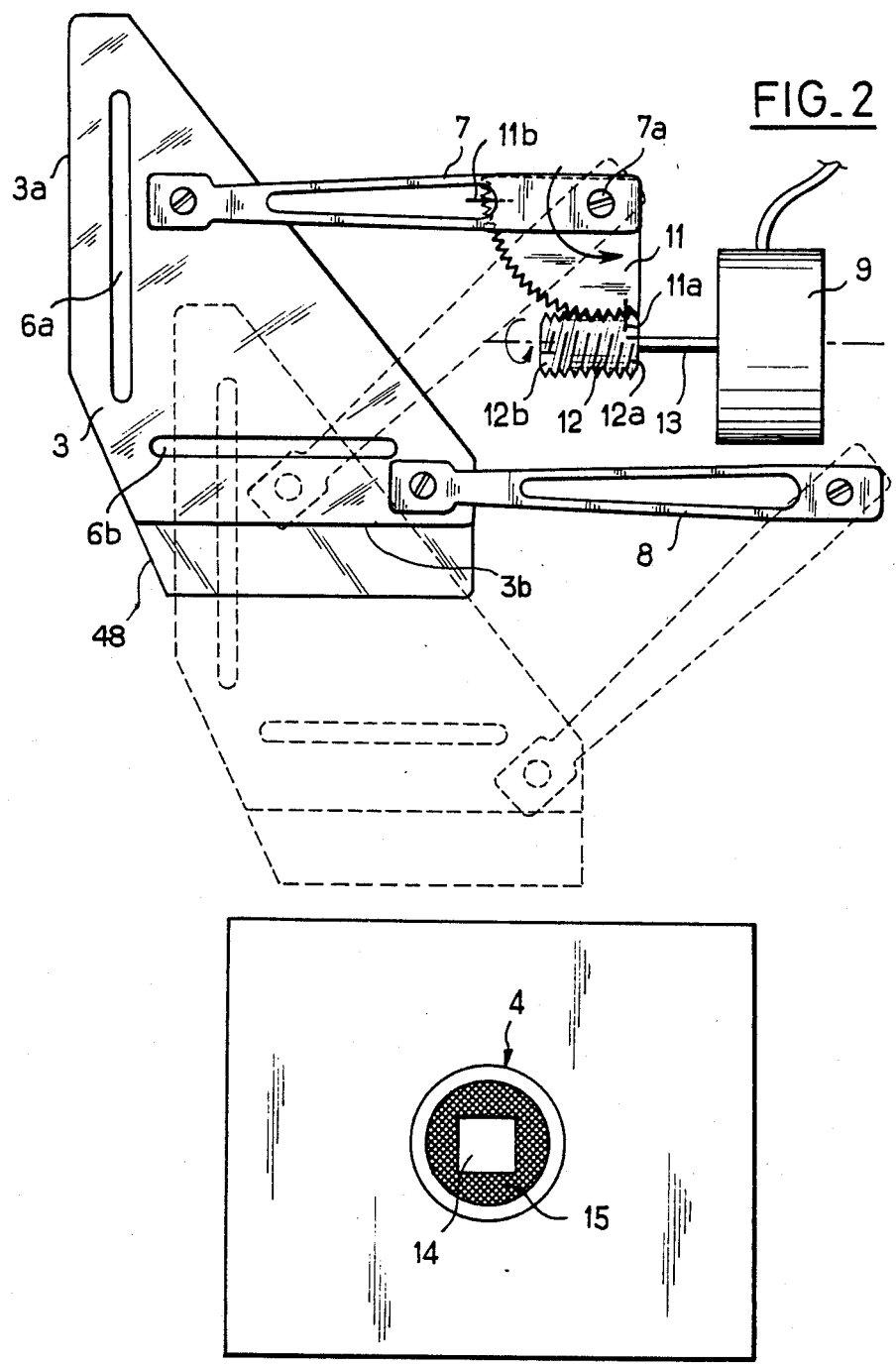
FIG. 2 is a partial plan view of the device according to the invention, showing the mechanism for moving a polarizing screen.
FIG. 3 is a plan view of the target placed in front of the device according to the invention.

In the embodiment shown in FIGS. 1 and 2, each polarizing screen 2, 3 is connected to holder 1 by two parallel arms 7, 8 jointed to the screen and to holder 1, and the pivot 7a is connected to a motor 9 (or 10) so as to be rotated.

As FIG. 2 shows, pivot 7a is secured to a toothed sector 11 engaging an endless screw 12 mounted on the output shaft 13 of motor 9 (or 10). At its two ends, the toothed sector comprises two catches 11a, 11b extending from the teeth and adapted to make tangential contact with lugs 12a, 12b mounted along the axis of the endless screw, so as to prevent the screw threads from becoming blocked at the end of the reciprocating travel of the polarizing screens. These or other abutments can be provided for limiting the motion of screens 2, 3 between a position (FIG. 2) where arms 7, 8 are substantially horizontal and a position (chain-line) where arms 7, 8 are inclined downwards.

In the first position, the bottom edge 2b or 3b of screens 2, 3 is disposed above the direction of vision of both eyes. Each screen 2, 3 can be moved from the aforementioned first position to a second position where slot 5b, 6b near the bottom edge 2b, 3b of each screen is in the direction of vision of the corresponding eye when facing the target 4, and to a third position where slot 5a, 6a near the side edge 2a, 3a of each screen 2, 3 is in the aforementioned direction of vision.

The electric motor 9, 10 for driving screens 2, 3 is associated with means for locating the position of slot 5b, 6b near the bottom edge 2b, 3b of each screen 2, 3 with respect to a horizontal reference axis on holder 1 extending through the middle thereof. The means can also locate the position of the slot 5a, 6a near the side edge of each screen 2, 3 relative to a reference position perpendicular to the previously-mentioned reference and extending through the axis of symmetry Y—Y' of holder 1 extending between the two polarized screens 2, 3.

Preferably the electric motor 9, 10 is of the stepping kind and the aforementioned means comprise known means for counting the number of revolutions of motor 9, 10 and converting the number into the distance travelled by screen 2, 3 relative to the aforementioned reference axes. The motor can be of a different kind, using suitable motion-monitoring means.

As FIG. 3 shows, target 4 at its centre has an e.g. square light source 14 covered by a polarizing screen (not shown) having an axis of polarization perpendicular to that of the polarizing screens 2, 3 borne by holder 1. Source 14 is surrounded by a dark area 15 or a non-polarized illuminated area mounted on a pivoting device. The brightness of source 14 and area 15 is adjustable.

The device according to the invention comprises a switch 32 (see FIG. 9) for actuation by the patient wearing the device so as to provide information to a monitoring device 35, when modifications occur in visual sensations of the aspect of source 14 of target 4 during motion in front of the patient's eyes, of the polarizing screens 2, 3 comprising slots 5a, 5b, 6a, 6b driven by motors 9, 10 secured to holder 1.

Figure 4:
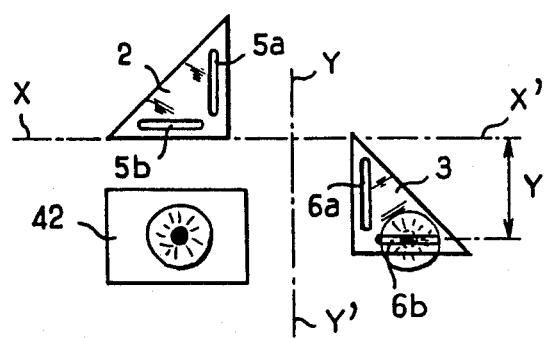
FIGS. 4 and 5 are diagrammatic views showing the operation of the device according to the invention.

Device 35, via switch 32, can switch off the light source 14 as soon as the patient begins to perceive it, for the time during which the slot is travelling through the field of vision, the motor is then switched off by device 35 and the source is automatically re-energized by order of the monitoring device when the eye is hidden by the polarizing part of the screen. Holder 1 can also bear two opaque shutters 42 (see FIGS. 4 and 5) which can be lowered on to each of the patient's eyes, depending on the examination for which the device is used, as will be shown in detail hereinafter.

Holder 1 comprises means for securing it to test spectacles for examination of binocular vision.

Alternatively, holder 1 can be independent and comprise means for directly securing it in front of the patient's eyes without interposed spectacles, and means for securing corrective lenses to holder 1.

In the example shown in FIG. 1, holder 1 comprises means for securing it to the patient's spectacle frame 16. The means comprise supports 17, 18 to which supports 19, 20 are secured. Supports 19, 20, can be in the form of washers adapted to be inserted into the grooves at the top of the circles of the frame. The spacing between supports 19, 20 is adjustable via supports 17, 18 so as to adapt to the spacing of the frame in FIG. 1, so that the device can be secured to all sizes of spectacles. Two levers 36, 37 extend in front of the frame and at their ends have shafts 38, 39 perpendicular to the levers and covered with non-slipping material, and bear via springs 40, 41 on the inner surface of the frame. The frame is gripped between washers 19, 20 and shafts 38 and 39.

Frame 16 is centred relative to holder 1 by means of a lug 21 secured to holder 1 so as to be slidable along the axis of symmetry Y—Y' thereof, the bottom part 21a of the lug resting in a notch 22 at the top of frame 16.

Holder 1 also has a flexible strap or belt 23 secured to the ends of holder 1 and adapted to be passed around the patient's head so that holder 1 becomes completely steady.

We shall now describe the operation of the device according to the invention, which is used for detecting and measuring anomalies in binocular vision.

The device when used for this purpose need not be secured to a frame chosen by the patient, and therefore is either independent or secured to a test frame comprising a test-lens holder.

Anomalies in binocular vision are measured in two steps.

Firstly, the device according to the invention is used to measure the position of the axis of vision of each eye separately, when the other eye is blocked by an opaque shutter. Target 4 is placed at a considerable distance (at least 5 meters) from the patient. When binocular vision is shut off, the axes of vision of both eyes are substantially parallel.

The two polarizing screens 2, 3 are raised above the horizontal reference axis X—X' (see left part of FIG. 4) extending through the middle of support 1. The patient clearly sees the light source 14 with both eyes. Screens 2, 3 are then lowered together until their bottom edges 2b, 3b intersect the axes of vision towards the source 14, which is no longer visible by the patient.

An opaque shutter 42 is then used to cover one eye so as to measure the position of the axis of vision of the other eye. The patient is then asked to state whenever the light source 14 appears in front of the eye not covered by the opaque shutter.

One polarizing screen (e.g. screen 3) is lowered (see right part of FIG. 4) until the bottom edge of the horizontal slot 6b intersects the axis of vision. At this moment, the light source 14 appears and the patient actuates a switch which, via a monitoring device, extinguishes the light source and shortly after disconnects motor 9, so that the slot has passed in front of the eye which is again blocked by part of the polarizing screen. When the light is put out by the switch, a first measurement is made of the travel of screen 3 along Y—Y'. At this moment the source is re-illuminated but invisible to the eye behind the polarizing screen. The motor is then reversed and screen 3 rises until source 14 reappears, i.e. when the top edge of the horizontal slot 6b intersects the axis of vision. The patient actuates the switch which, via the monitoring device, puts out the light source 14 and a few moments later stops the motor, after the time needed for the polarizing screen to move in front of the eye and again cover it. When the light is put out by the switch, a second measurement is made of the travel of screen 3 along Y—Y'. The average of the aforementioned two measurements gives the position Y of the axis of vision of a first eye relative to the reference axis X—X'. The eye is then covered by the opaque shutter 42. The various aforementioned positions of screen 3 are diagrammatically shown in FIG. 6. The same measurements are then made on the other eye.

Figure 5:
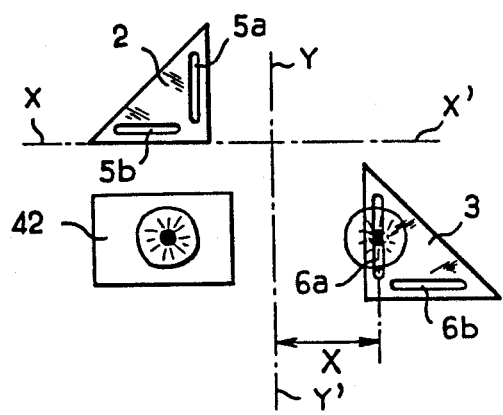

The same method is then used to determine the position for each eye of the axis of vision relative to the vertical reference axis Y—Y', and a measurement X is deduced therefrom (see FIG. 5).

Values X and Y can be used to determine the position of the axes of vision of the patient's eyes during monocular vision.

Secondly, the device according to the invention can be used to measure the position of the directions of vision of each eye during binocular vision, when the opaque shutter 42 is raised. Care must be taken beforehand to place dissociating lenses on the test spectacles, as normally used in this kind of examination.

The Maddox rod examination or streaked Bagolini lenses examination can be used for this purpose.

The two polarizing screens 2, 3 are raised above the horizontal reference axis X—X', after which screens 2, 3 are lowered together until the bottom edges 2b, 3b thereof intersect the directions of vision towards the light source 14, which is no longer visible to the patient.

During the vision test, target 4 is as before disposed five meters in front of the patient and the measurements are the same as before, except that the fixed polarizing screen is placed in front of the eye which is not measured.

Two positions of the axis of vision, for vision at infinity, are obtained for each eye in order to deduce whether there is an anomaly if the axis of vision during binocular vision is deflected from the position thereof when interrupted by the opaque shutter. The anomaly can then be measured.

In another application, the device can be attached to a spectacle frame chosen by the patient and, in the absence of any anomaly in binocular vision, can be used to locate the axis of distant and near vision. The measurements are made by the same method as before, without using an opaque screen or dissociating lenses, the non-measured eye being covered by the polarizing screen. In this application, the horizontal reference axis X—X' extends through the points of intersection of the circumference of washers 19, 20 with the perimeter of the outline of the frame at the bottom of the groove. The height of the axis of vision starts at the aforementioned point of intersection on the central axis of the outline, after the device has been adjusted when separate from the frame.

The main advantages of the invention are as follows:

Dialogue with the patient is at a minimum, so that the risk of errors is greatly limited and the measurements take much less time;

The measurements are very accurate, and

The device is suitable for all examinations of anomalies in binocular vision.

Target 14, instead of being placed at a considerable distance from the patient for distant vision (which is not always possible in a small room) or at a short distance for near vision, can be placed near the device shown in FIGS. 7 and 8.

In FIGS. 7 and 8, the device comprises a casing 24 disposed at a certain distance in front of the patient's eyes 25. The casing has an opening 26 directed towards the eyes 25. The bottom edge 27 of opening 26 bears the target 4. The end of casing 24 remote from opening 26 has a flat reflecting surface, e.g. a plane mirror 28 disposed at an angle of 45° to the patient's direction of vision 29. The upper inner surface of casing 24 comprises a spherical reflecting surface 30 having its concavity facing the interior of casing 24. The plane mirror 28 intersects the principal axis 46 of mirror 30 half way along the focal length thereof.

The image 31 of target 4 relative to mirror 28 occurs at the focus of mirror 30. All light rays from target 14, after double reflection at mirror 28, are parallel when they leave casing 24, so that target 4 appears to the patient to be at infinity.

In order to obtain different observation distances, inter alia for examining close vision, it is only necessary to move target 4 (see arrow F in FIGS. 7 and 8) towards the principal axis 42 of mirror 30 along a straight line perpendicular thereto, towards the intersection of mirror 28 with the principal axis of the concave mirror.

In the diagram in FIG. 9, a relay box 33 connects the light source 14 to switch 32, to the holder 1 comprising the electric motors 9, 10 for driving the screens 2 and 3, and to the monitoring device 35 which includes a micro-computer 34 having display means 47 comprising a display screen and printer and capable of calculating the travel of screens 2, 3, converting the travel into positions expressed in suitable units such as dioptres or prismatic degrees, and displaying the resulting units.

Accordingly, the micro-computer 34 directly indicates any anomalies found by the device according to the invention and forecasts the corrections which have to be made to the patient's sight.

Of course, the invention is not limited to the previously-described embodiments and can be modified in numerous ways without departing from its scope.

For example, holder 1 can comprise means other than parallel arms 7, 8 for ensuring that when screens 2 and 3 move, slots 5a, 6a and 5b, 6b remain parallel to themselves, i.e. always vertical and always horizontal respectively.

For example, arms 7, 8 can be replaced by a pivoting lever driven in rotation by a motor and secured to a toothed wheel engaging a second toothed wheel secured to the lever and having its shaft jointed to screen 2 or 3.

In another variant, a pivoting lever driven in rotation by a motor comprises a disc secured to the motor axis, the disc circumference having a joint connected to a rod which in turn is jointed to a disc borne by the arm having a pivot jointed to screen 2 or 3.

In another variant, one end of a lever is connected to the motor shaft. The other end of the lever is jointed to the polarizing screen 2 or 3. Perpendicular rods are connected to screen 2 or 3 so as to be parallel to the vertical slot and horizontal slot respectively. The rod ends are guided in guides parallel to the horizontal slot and vertical slot respectively, so that the ends can slide in the corresponding guide when the lever pivots and so that the slots in screen 2 or 3 remain parallel to themselves.

Of course means other than those briefly described are also possible.

Also, the shutters 42 borne by holder 1 for lowering over each eye can be replaced by masks separate from holder 1, or by an opaque strip 48 disposed near the bottom edges 2b, 3b of screens 2, 3 (see FIG. 2).

We claim:

1. An optical device for measuring the position of the main or other directions of vision of the two eyes of a patient using the device and for measuring anomalies in binocular vision, the device being adapted for fitting in front of the patient's eyes and comprising a holder (1) bearing two movable screens (2, 3) of transparent polarizing material, means for moving the two screens (2, 3) in front of the eyes, means for locating the position of the screens relative to the holder (1), and a target (4) separated from the holder and adapted to be placed in front of the patient so as to be visible to the patient, said target (4) comprising a central area having an axis of a polarization perpendicular to that of the polarizing screens (2, 3), characterized in that each polarizing screen (2, 3), adjacent its side edge (2a, 3a) nearest to the axis of symmetry of the holder (1) extending between the two screens, contains a first slot (5a, 6a) substantially parallel to said axis of symmetry and adjacent its bottom edge (2b, 3b) contains a second slot (5b, 6b) substantially perpendicular to said first slot and said means for moving the two screens (2, 3) comprises a single actuating assembly for each screen and transmission means (7, 8) such that said first and second slots (5a, 6a; 5b, 6b) in the screens remain parallel to themselves, respectively, when the screens move.

2. A device according to claim 1, characterized in that each polarizing screen (2, 3) is connected with the holder (1) by two parallel arms (7, 8) jointed to the screen and to the holder and in that a pivot (7a) joining one of the arms (7, 8) to the holder (1) is connected with the corresponding single actuating assembly which comprises a motor (9, 10) for rotating the pivot.

3. A device according to claim 2, characterized in that the pivot (7a) is secured to a toothed sector (11) which at its two ends comprises two lugs (11a, 11b) engaging an endless screw (12), each end of which comprises a stop (12a, 12b) mounted on the output shaft (13) of the motor (9, 10).

4. A device according to claim 1, characterized in that the means for moving the two screens (2, 3) and the transmission means are adapted to move the two screens (2, 3) between a first position where the bottom edges (2b, 3b) of the screens (2, 3) are disposed above the direction of vision of the two eyes, a second position in which said second slots (5b, 6b) situated near the bottom edge (2b, 3b) of each screen are in the direction of vision of the corresponding eye when turned towards the target (4), and a third position in which said first slots (5a, 6a) near the side edge (2a, 3a) of each screen are in said direction of vision.

5. A device according to claim 4, the single actuating assembly for moving each polarizing screen (2, 3) between said first, second and third positions comprising an electric motor (9, 10), characterized in that the electric motor (9, 10) is connected with locating means by means of which the position of said second slot (5b, 6b) near the bottom edge (2b, 3b) of each screen (2, 3) is located with respect to a horizontal reference axis (X—X') extending through the middle of the holder (1) or extending through reference points of two supports (19, 20) having an adjustable spacing, said locating means being also adapted to locate the position of said first slot (5a, 6a) near the side edge (2a, 3a) of each screen with respect to the axis of symmetry (Y—Y') of the holder situated between the two polarizing screens (2, 3).

6. A device according to claim 5, characterized in that said electric motor (9, 10) is a stepping motor and said locating means comprises means for counting the number of revolutions of the motor and for converting the number into the distance through which the screens (2, 3) have moved.

7. A device according to claim 1, characterized in that the target (4) is pivotable and at its center comprises a light source (14) covered by a polarizing screen having an axis of polarization perpendicular to that of the polarizing screens (2, 3) borne by the holder (1), the light source being surrounded by a non-polarized reference area (15) of adjustable brightness.

8. A device according to claim 7, and further comprising an information transmitting switch (32) for actuation by the patient wearing the device so as to supply a monitoring device (35) with information regarding detection and modifications of sensations of light, so as to determine the supply of electric power to the electric motors (9, 10) and the source (14) and to move the polarizing screens (2, 3) borne by the holder (1).

9. A device according to claim 8, characterized in that the light source (14) of the target (4), the information-transmitting switch (32) and the electric motors (9, 10) actuating the polarizing screens (2,3) are connected by a relay box (33) to the monitoring device (35) which comprises a micro-computer (34) having display means (47) and capable of calculating the displacement of the polarizing screens (2, 3), converting said displacement into positions expressed in suitable units and displaying the corresponding values.

10. A device according to claim 1, characterized in that the holder (1) bears at least one of opaque shutters (42) and strips (48) arranged at the bottom of the polarizing screens (2, 3) in front of each eye of the patient.

11. A device according to claim 1, characterized in that the holder (1) comprises means for securing it to test spectacles for examinations of binocular vision.

12. A device according to claim 1, characterized in that the holder (1) is independent and comprises means for securing it directly in front of the patient's eyes, without interposed spectables, and means for securing corrective lenses to the holder (1).

13. A device according to claim 1, characterized in that the holder (1) comprises means (17, 18, 19, 20, 36, 37, 38, 39) for securing it to the patient's spectacle frame.

14. A device according to claim 1, characterized in that it comprises a casing (24) adapted to be placed at a certain distance in front of the patient's eyes (25), said casing having an opening (26) directed towards the patient's eyes, the bottom edge (27) of the opening bearing the target (4), the end of the casing (24) remote from said opening having a flat reflecting surface (28) intersecting the principal axis (46) of a concave mirror (30) at a distance equal to half the focal length of the concave mirror and at an angle of 45° towards the concavity of the mirror.

* * * * *